(12) United States Patent
White et al.

(10) Patent No.: US 6,472,675 B2
(45) Date of Patent: Oct. 29, 2002

(54) CONTAINER FOR STORING AND SHIPPING NEEDLE CARTRIDGES

(75) Inventors: Jack White, Alpharetta, GA (US); John R. Vinson, Decatur, GA (US)

(73) Assignee: Theragenics Corporation, Buford, GA (US)

( * ) Notice: Subject to any disclaimer, the term of this patent is extended or adjusted under 35 U.S.C. 154(b) by 28 days.

(21) Appl. No.: 09/737,412

(22) Filed: Dec. 15, 2000

(65) Prior Publication Data

US 2002/0074525 A1 Jun. 20, 2002

(51) Int. Cl.$^7$ ............................................. G21F 5/015
(52) U.S. Cl. ............................ 250/506.1; 600/7; 600/8
(58) Field of Search ........................ 250/507.1, 506.1; 600/7, 8

(56) References Cited

U.S. PATENT DOCUMENTS

| | | | |
|---|---|---|---|
| 1,576,535 A | 3/1926 | Muir | |
| 3,256,441 A | 6/1966 | Grasty | |
| 3,744,661 A | 7/1973 | Fischer, Jr. | 220/21 |
| 3,882,315 A | 5/1975 | Soldan | 250/506 |
| 4,151,912 A | 5/1979 | Harrold | 206/338 |
| 4,240,547 A | 12/1980 | Taylor | 206/204 |
| 4,501,360 A | 2/1985 | Levy et al. | 206/443 |
| 4,759,345 A * | 7/1988 | Mistry | 250/507.1 |
| 4,783,309 A | 11/1988 | Popp et al. | 376/272 |
| 4,808,831 A | 2/1989 | Whiddon | |
| 4,826,003 A | 5/1989 | Levy | 206/45.31 |
| 4,846,235 A * | 7/1989 | Handke | 250/506.1 |
| 4,847,505 A | 7/1989 | Suthanthiran | 250/507.1 |
| 4,932,533 A | 6/1990 | Collier | 206/569 |
| 4,997,090 A | 3/1991 | Lenmark, Sr. et al. | 206/570 |
| 5,460,592 A | 10/1995 | Langton et al. | 600/7 |
| 5,828,073 A | 10/1998 | Zhu et al. | |
| 5,829,589 A | 11/1998 | Nguyen et al. | 206/366 |
| 5,860,909 A | 1/1999 | Mick et al. | 600/7 |
| 6,323,501 B1 * | 11/2001 | White et al. | 250/507.1 |

OTHER PUBLICATIONS

Copy of p. 1 of European Search Report for corresponding PCT application No. PCT/US01/02444 and 2 pages of Documents Considered to be Relevant.

* cited by examiner

Primary Examiner—Jack Berman
(74) Attorney, Agent, or Firm—Knoble & Yoshida, LLC

(57) ABSTRACT

A container for storing and transporting needle cartridges containing radioactive materials used for medical procedures is disclosed. Such needle cartridges may include a radioactive shielding material which contains a portion of the radioactivity emitted by the radioactive material. The container of the present invention has an upper portion and a lower portion, and at least one of the portions includes a radiation shielding material, such as lead, steel or other appropriate shielding materials. Needle cartridges containing radioactive material are placed within the container for storage and shipping. The container secures the needle cartridges against lateral movement within the container to protect them from breakage or release of the radioactive materials contained in the needle cartridges. The radiation shielding material of the lower portion of the container may cooperate with the radiation shielding material of the device to container more of the emitted radiation that is contained by the device alone. The container and the holder may be sterilizable to allow such devices to be transported in sterilized form for medical use.

10 Claims, 6 Drawing Sheets

CONTAINER FOR STORING AND SHIPPING NEEDLE CARTRIDGES

FIELD OF THE INVENTION

The present invention relates to containers for the storage and transportation of devices which contain radioactive material, preferably for shipping of needle cartridges containing radioactive seeds used for medical treatments.

BACKGROUND OF THE INVENTION

Radioactive materials may be used for treating various illnesses including tumors and nodules. For example, radioactive materials, such as iodine$^{125}$, palladium$^{103}$, or the like, may be implanted into a patient to provide localized radiation treatment of tumors.

It will be appreciated that such radioactive materials must be stored and transported in containers which protect patients, medical personnel and others that must handle the radioactive materials from unnecessary exposure to radiation. Additionally, the radioactive materials must be packaged to allow safe transport from the manufacturer to an end user. Further, such radioactive materials must be safely packaged for storage at a facility, such as a warehouse or a hospital.

Conventional containers for transporting devices containing radioactive material are generally made of lead or steel or some other radiation shielding material. These containers, however, may be large, awkward and heavy. Shipping such containers may be difficult, thereby increasing costs for the radioactive material, and discouraging return, cleaning and/or reuse of the containers.

One such existing container is made from a large block of steel having a handle formed integrally therewith. Within the steel block are formed a number of cylindrical cavities each for receiving a magazine containing radioactive seeds. Such steel containers are inordinately heavy and cumbersome and do not provide complete shielding of the radiation which escapes from the magazine.

Additionally, it is often necessary to sterilize medical equipment before use. The large size and weight of existing containers for magazines of radioactive seeds make them awkward to clean and/or sterilize. Also, these containers are unwieldy for handling the small quantities of radioactive material used in individual surgical procedures.

These and other drawbacks for presently available containers exist.

SUMMARY OF THE INVENTION

An object of the present invention is to overcome these and other drawbacks in existing containers.

Another object of the present invention is to provide a convenient, relatively lightweight container for storage and transportation of radioactive materials.

Another object of the present invention is to provide a container for transporting and storing devices housing radioactive material, wherein the container and the device cooperate to provide radiation shielding.

Another object of the present invention is to provide a container for transporting and storing devices housing radioactive material, whereby the devices are secured within the container to resist movement during transport and use.

Another object of the present invention is to provide a container for transporting and storing devices housing radioactive material, wherein the container includes a separate device holder which may be sterilized within or apart from the radiation shielding container, thereby easing the process of sterilizing the devices for use.

Another object of the present invention is to provide a container for transporting and storing devices housing radioactive material, wherein the devices are sealed within the container of the invention in a sterilized condition, thereby enabling transportation of sterilized devices.

These and other objects of the invention are accomplished according to various embodiments of the invention. One embodiment of the invention provides a container for storage and transportation of one or more devices each containing a plurality of individual dosage units of radioactive material. The container also includes structure for securing the devices for transport. The container of the present invention is designed such that it acts to contain at least some of the radiation emitted by the stored radioactive material.

DETAILED DESCRIPTION OF THE PREFERRED EMBODIMENTS

The container of the present invention may be used for storage and transportation of one or more needle cartridges housing radioactive materials. Nonetheless, the structures and characteristics of the invention are equally applicable to the storage and transport of other devices including radioactive material, as well.

Specific embodiments of the present invention, as will be illustrated further in FIGS. 1–4, provide a container for the storage and transportation of needle cartridges containing radioactive material. Radioactive seeds, which are used in the treatment of tumors and other medical problems, are often dispensed using needle cartridges which generally contain a plurality of such seeds. The needle cartridges function to both contain a large number of seeds in an easy to use manner and to provide a convenient way to dispense the seeds when needed for treatment. Such needle cartridges typically dispense one seed at a time in a predetermined manner and orientation for use. The present invention is designed to store a variety of conventional needle cartridges.

Figure 1:
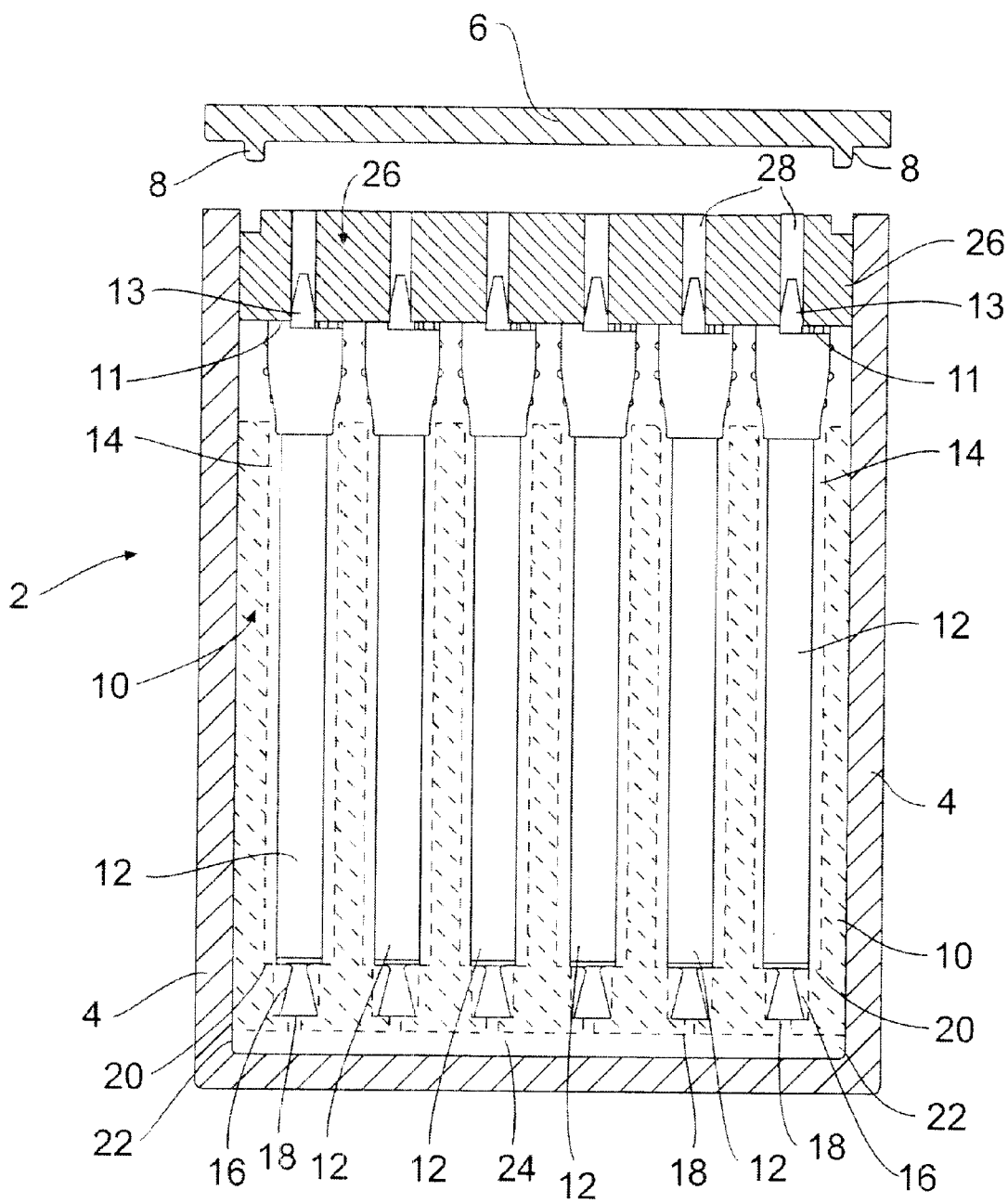
FIG. 1 is a cross-sectional view of a container for needle cartridges according to a first embodiment of the invention.
Figure 2:
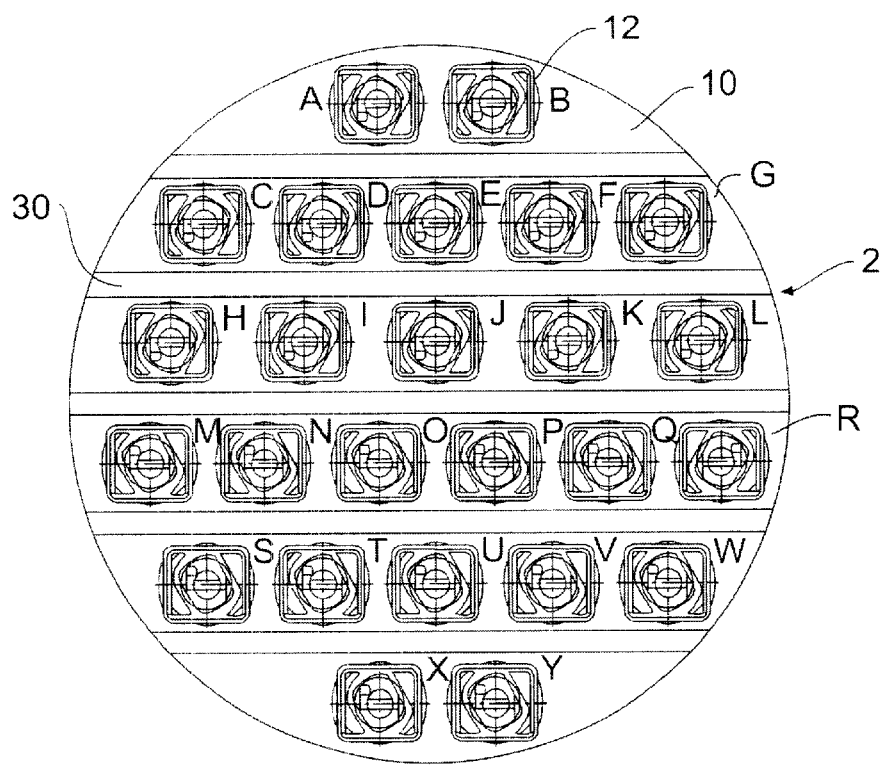
FIG. 2 shows a top view of the container of FIG. 1 with the top and foam or plastic inserts removed.

FIGS. 1 and 2 illustrate a first embodiment of a container 2 according to the invention for storing and transporting one or more needle cartridges 12 containing radioactive materials. Container 2 includes a lower portion 4 and a top 6. In the preferred embodiment of the present invention lower portion 4 and top 6 are separate elements which can be taken apart to allow access to the inside of container 2. Lower portion 4 may include a conventional radiation shielding material, such as lead, steel or other appropriate materials. In a more preferred embodiment, both top 6 and lower portion 4 of container of 2 include a radiation shielding material. Top 6 may be fitted into place on lower portion 4 of container 2 by virtue of a lip 8 which extends around the periphery of top 6 and fits snugly within the inside edges of container 4 as shown in FIG. 1. The closure is preferably a friction fit or slip-fit, although it is also possible to use mechanical fasteners, threads, or other similar closing structures in order to affix the top 6 to the lower portion 4 of the container of the present invention. The container may also further be taped closed on the outside to provide additional security, and such tape may also contain a radiation shielding material.

A basket 10, which serves as a holder for needle cartridges 12, is located within lower portion 4 of container 2 as shown in FIG. 1. Basket 10 also functions to isolate needle cartridges 12 from contact with the lower portion 4 of container 2. Such isolation may be required depending on the material used to fabricate lower portion 4 of container 2. Also, it may be desirable to isolate needle cartridges 12 from container 2 so that it is not necessary to sterilize container 2 for each use. Instead, basket 10 can be removed and sterilized for each use thereby facilitating easy sterilization of the transport container.

Needle cartridges 12 may be placed in recesses 14 of basket 10. Optionally a drain port 18 may be located in the bottom of each recess 14 of basket 10 to allow liquids to drain from recesses 14 in order to facilitate cleaning and sterilization of basket 10. The desirability of a drain port 18 will depend on whether it is necessary to maintain complete isolation between the lower portion 4 of container 2 and basket 10 or whether it is possible to allow some contact of liquids with lower portion 4 of container 2 via drain port 18.

Recesses 14 may be customized to conform to the specific shape of the needle cartridges 12 or to help properly align needle cartridges 12 in recesses 14 during insertion, such as, for example by providing a narrower section of recesses 16 formed by a shoulder 20. Narrower portion 16 of recesses 14 can also provide a friction fit, snap fit or slip-fit for needle cartridges 12 in order to more securely hold them in position in the shipping container 2 for shipment and storage.

Basket 10 may also include a downwardly protruding lip 22, as shown in FIG. 1 in order to maintain a space 24 between basket 10 and lower portion 4 of container 2. Space 24 in conjunction with drain ports 18 provides an area where liquid can drain into the bottom of container 2, if desirable.

In order to secure needle cartridges 12 in basket 10, it is preferable to employ a foam or plastic insert 26 which is located atop needle cartridges 12 once they are in basket 10. Foam or plastic insert 26 may be a single piece of foam or plastic which includes a plurality of channels 28 therein for receiving the tips 13 of needle cartridges 12. Alternatively, foam or plastic insert 26 can be formed from a plurality of individual piece of foam or plastic, each of which covers either a single needle cartridge or several needle cartridges. Individual pieces of foam or plastic are preferred since a single needle cartridge 12 can be exposed at a time while leaving the remaining needle cartridges 12 secured in basket 10. Foam or plastic insert 26 is designed to rest against the top surface of needle cartridge shoulders 11 as shown in FIG. 1.

Referring now to FIG. 2, there is shown a top view of the container 2 in accordance with the present invention with the top 6 removed. The container 2 shown in FIG. 2 is fully loaded with needle cartridges 12. As shown in FIG. 2, basket 10 preferably includes reinforcing ribs 30 to provide additional structural integrity to basket 10. As can be also seen from FIG. 2, container 2 can hold up to twenty-five needle cartridges 12 in the embodiment shown, although container 2 can be designed to hold more or less cartridges 12, as desired.

In a preferred embodiment of the invention basket 10 is made of a sterilizable material. Basket 10 may be removed from container 2, and be separately placed in a sterilization unit such as an autoclave or chemical disinfection, chemical sterilization or other conventional means of sterilization, or may be sterilized while within lower portion 4 of container 2. Basket 10 may optionally be provided with a handle (not shown) to facilitate removal and replacement of basket 10 in container 2. Thus, basket 10 may act as a simple transfer device for handling one or more needle cartridges 12 prior to, and during use. Basket 10 may be injection molded from, for example, nucleated polypropylenes, polysulfones, polycarbonates, high temperature acrylics or polyether sulfones. Other conventional materials and/or methods of making basket 10 may also be employed. In an alternative embodiment, container 2 may itself be sterilized, such as by an autoclave or other conventional means, thereby allowing sterilized needle cartridges 12 to be sterilized directly in container 2 or stored or transported in container 2 in a sterilized condition.

Basket 10 of container 2 allows needle cartridges 12 to be transported and sterilized easily, e.g., within a medical facility. Ease of transportation helps minimize handling, thereby reducing the potential for exposure to radiation. A lightweight basket 7 also reduces the overall weight of container 2, thereby reducing transportation costs and facilitating the handling of container 2. In an alternative, less preferred embodiment, basket 10 may be formed integrally with container 2.

Figure 3:
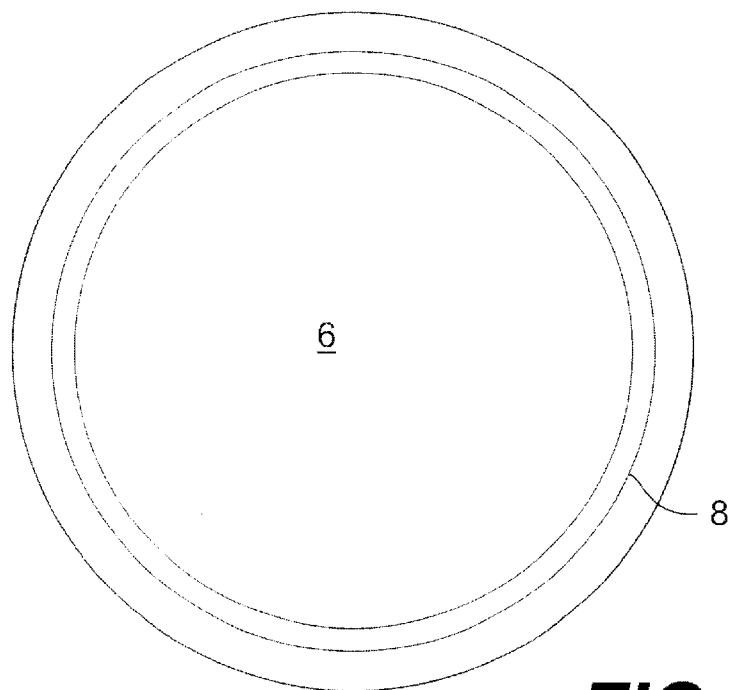
FIG. 3 shows a view of the bottom side of the top for the container of FIG. 1.

Referring now to FIG. 3, there is shown an underside view of top 6 of container 2. From this view it is possible to see circumferential lip 8 of top 6. Other suitable tops 6 may be employed and circumferential lip 8 need not extend completely around the circumference of top 6 although it is preferred to do so.

To use the container shown in FIGS. 1-3, one or more needle cartridges 12 containing radioactive material are placed in recesses 14 of basket 10. Basket 10 is then located in lower portion 4 of container 2. In this configuration, without top 6 the radiation shielding material included in lower portion 4 may cooperate with radiation shielding of needle cartridges 12, if applicable, to together contain a substantial portion of the radiation emitted by the radioactive material when the needle cartridge 12 is the type which includes its own radiation shielding material. Thus, even with the top 6 taken off, the potential for exposure to radiation, is minimized due to either the radiation shielding of the lower portion 4 of container 2 or to the cooperative shielding provided by the radiation shielding of needle cartridges 12 and the lower portion 4 of container 2.

Figure 4:
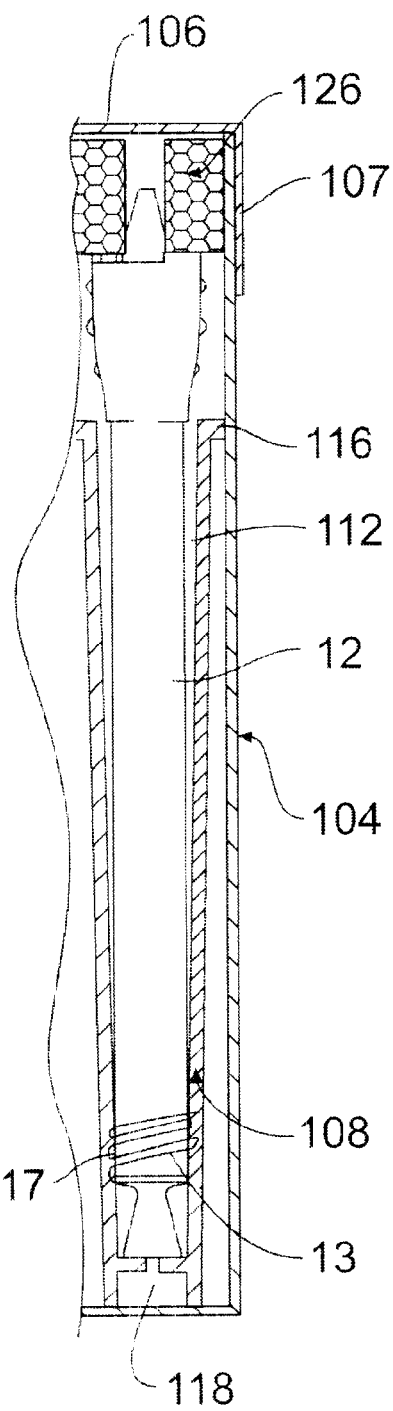
FIG. 4 shows a cross-sectional view of a portion of a container according to a second embodiment of the present invention to illustrate an embodiment employing threads.

Needle cartridges 12 may be fitted into recesses 14 of lower portion 4 by a friction fit, mechanical fastener, slip-fit or by a thread 17, provided on the inner surface of each recess 14 and a cooperating thread 13 provided on the outer surface of needle cartridges 12, as shown, for example, in FIG. 4. Subsequently, top 6 is fitted onto lower portion 4 such that the circumferential lip 8 fits snugly within lower portion 4 to hold top 6 in place in lower portion 4. Before top 6 is put on, foam or plastic insert 26 is positioned atop needle cartridge shoulder 11 to secure the needle cartridges 12 to minimize or prevent vertical movement of needle cartridges 12 within recesses 14 during storage and transport. Top 6 may also optionally include a radiation shielding material to provide additional shielding against radiation emitted in the vertical direction from needle cartridges 12.

Figure 5:
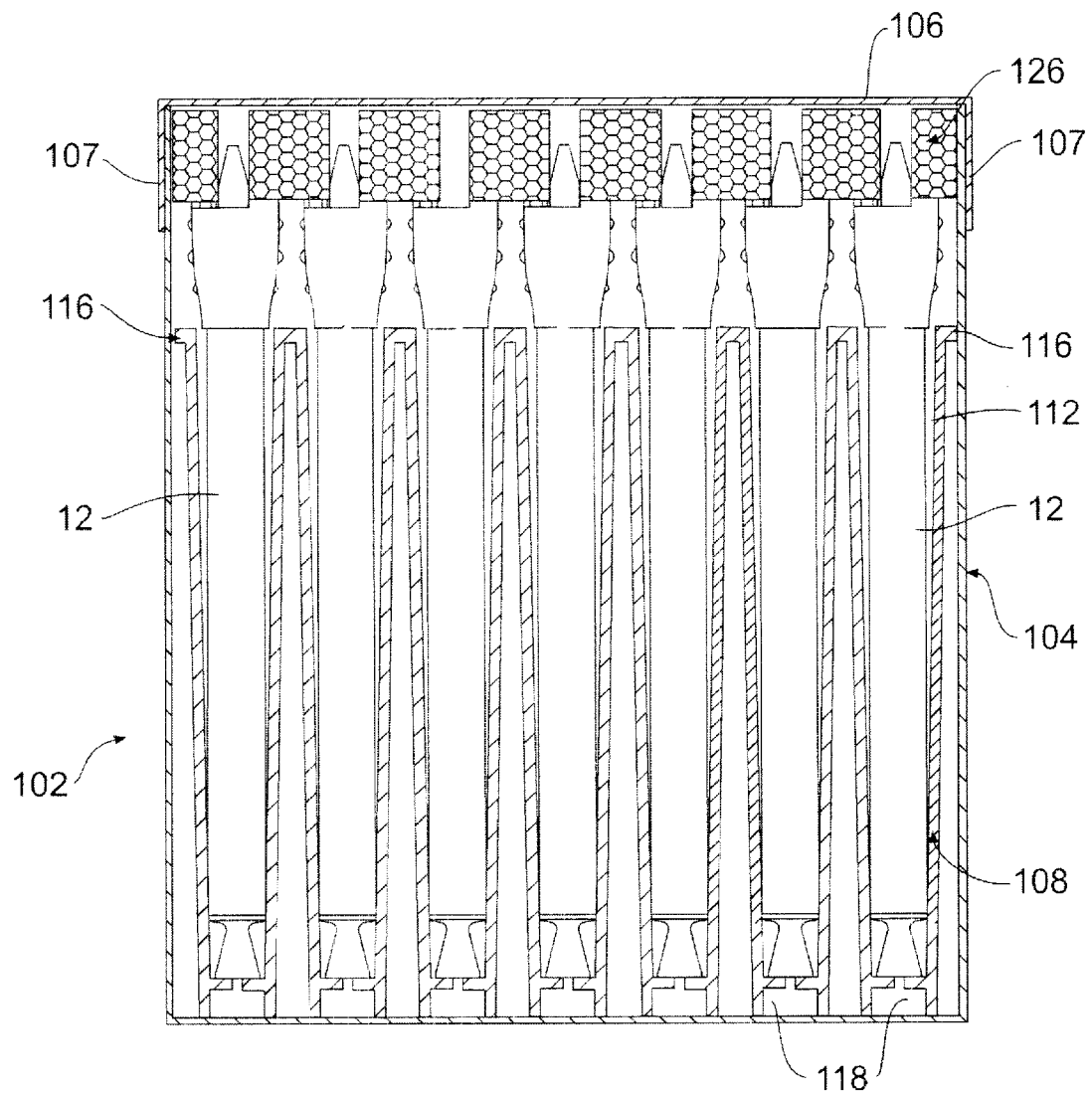
FIG. 5 shows a cross-sectional view of a container according to a second embodiment of the present invention.

FIG. 5 illustrates another embodiment of a container 102 of the present invention. Container 102 of FIG. 5 comprises a lower portion 104 and a top 106. Lower portion 104 preferably includes a conventional radiation shielding material, such as lead, steel or other appropriate materials. In a more preferred embodiment of the invention, both top 106 and lower portion 104 of container 102 include a radiation shielding material. Top 106 and lower portion 104 may be joined by a closure 107 such as a friction fit, a mechanical fastener, a slip-fit, threads or other similar closing structures. Tape may be provided on the outside of container 102 to ensure that the container 102 is not open during transport.

Basket 108 is designed to be placed within container 102. Basket 108 includes a plurality of recesses 112 for holding needle cartridges 12. Recesses 112 are preferably generally cylindrical in shape and more preferably are designed to provide a friction fit with at least a portion of a needle cartridge 12. Alternatively, recesses 112 are shaped to provide a form fit with needle cartridges 12. As shown in FIG. 5, recesses 112 are tapered such that recesses 112 form a friction fit with needle cartridges 12 over a bottom portion of needle cartridges 12. Recesses 112 thereby hold needle cartridges 12 by limiting their lateral movement within container 102 in order to prevent breakage or release of the radioactive material from the needle cartridges 12.

Basket 108 may be vacuumed-formed, molded or injection molded, for example, and is preferably made from plastic or other suitable material. Basket 108 may be made from, for example, nucleated polypropylenes, polysulfones, polycarbonates, high temperature acrylics or polyether sulfones.

Basket 108 stabilizes needle cartridges 12 during shipment and isolates needle cartridges 12 from direct contact with container 102. In a preferred embodiment of the invention, basket 108 is sterilizable. As such, basket 108 may be placed in a sterilization unit, such as an autoclave or other conventional sterilization means, to facilitate handling and sterilization of the needle cartridges 12 or may be sterilized together with container 102. Top 106 is preferably a slip-on lid as shown in FIG. 5 having a downwardly facing peripheral side portion 107 which fits snugly over the outer edge of container 102. Top 106 is shown in a bottom view in FIG. 7 to show the downwardly extending side portion 107.

Basket 108 may include drain ports 118 located in the bottom of each recess 112 of basket 108 to allow liquids to drain from recesses 112 to facilitate cleaning and sterilization of basket 108 including the inner surfaces of recesses 112. In addition, basket 108 may include a peripheral lip 122 to raise the bottom of basket 108 above the lower surface of lower portion 104 of container 102 as shown in FIG. 5 to provide a space where liquid may drain through drain ports 118. Basket 108 also preferably includes a circumferential lip 116 as shown in FIG. 5 which provides a friction or slip-fit with the inside edge of lower portion 104 of container 102.

Packing foam or plastic 126 may be employed to secure needle cartridges 12 in basket 108 as shown in FIG. 5. Packing foam or plastic 126 may be any suitable packing foam or plastic and may come in the forms described above for foam or plastic insert 26 of the first embodiment of the present invention.

Figure 6:
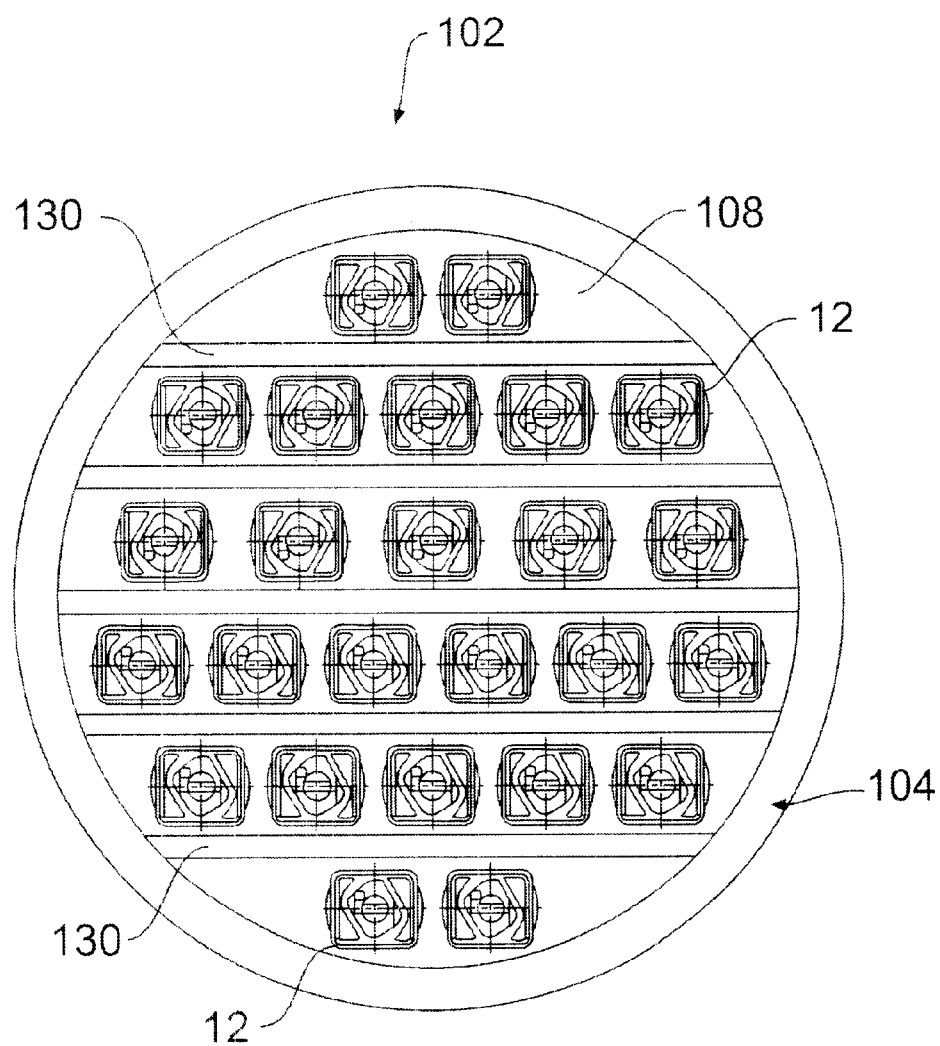
FIG. 6 shows a top view of the container of FIG. 3 with the slip-on lid and packing foam or plastic removed.

Referring now to FIG. 6, there is shown a top view of container 102 with the top 106 removed and which is completely filled with twenty-five needle cartridges 12. As shown in the figure, basket 108 may include a plurality of ribs 130 to provide structural integrity to basket 108. Basket 108 may accommodate twenty-five needle cartridges 12 in the embodiment shown although other suitable embodiments can include more or less needle cartridges 12 as desired.

Figure 7:
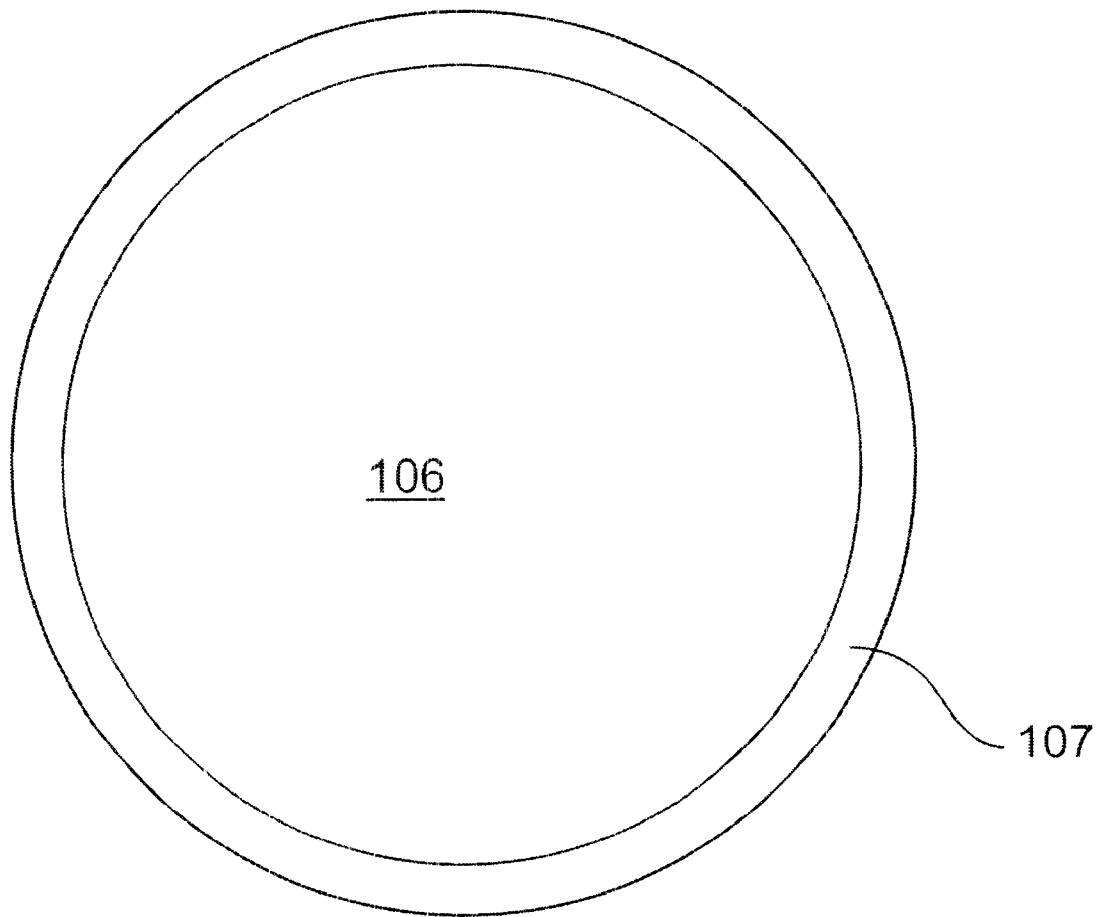
FIG. 7 shows a view of the bottom side of the top for the container of FIG. 5.

FIG. 7 shows a bottom view of top 106 showing the downwardly extending side portion 107 which extends around the circumference of top 106.

Container 102 may be used in the same manner as container 2 described above. Also, top 106 may include additional radiation shielding material in order to provide further shielding against radiation emitted in the vertical direction from needle cartridges 12.

These and other embodiments and uses of the invention will be apparent to those skilled in the art from consideration of the specification and practice of the invention disclosed herein. For example, containers may be altered to accept needle cartridges of various sizes and shapes. The specification and examples should be considered exemplary only. The scope of the invention is to be determined by the claims appended hereto.

What is claimed is:

1. A container for housing a plurality of needle cartridges containing radioactive materials therein, said container comprising:

a first portion which includes a radiation shielding material;

a second portion which, when associated with the first portion encloses the plurality of needle cartridges;

a structure for retaining the plurality of needle cartridges in said first position in a manner whereby the radiation shielding material of said first portion contains more of the radiation emitted by the radioactive materials than is contained by the needle cartridges themsleves, and wherein the structure for retaining the plurality of needles cartridges in the first portion of the container is separable from the first portion, and the structure limits lateral movement of the plurality of needle cartridges within the container.

2. A container as claimed in claim 1, wherein the structure for retaining the plurality of needle cartridges in the first portion comprises a basket including a plurality of recesses therein, each recess being adapted for retaining at least one needle cartridge therein.

3. A container as claimed in claim 1, wherein the structure for retaining the plurality of needle cartridges in the first portion includes a plurality of recesses for receiving and retaining a plurality of needle cartridges therein and wherein the container comprises a means for reasonably securing the plurality of needle cartridges in the plurality of recesses.

4. A container as claimed in claim 3, wherein said means for releasably securing the plurality of needle cartridges in the plurality of recesses is selected from a friction fit or a form fit between the plurality of recesses and the plurality of needle cartridges, a mechanical fastener, and a thread provided in the plurality of recesses which mates with a thread provided on the plurality of needle cartridges.

5. A container as claimed in claim 1, wherein the second portion of the container includes a circumferential lip which, when the second portion is associated with the first portion to close the container, provides a friction fit, form fit or slip fit between the second portion and the first portion to close the container.

6. A container as claimed in claim 1, wherein the second portion comprises a radiation shielding material.

7. A container as claimed in claim 2, wherein each recess is tapered to provide a friction fit, form fit or slip fit with a needle cartridge along a bottom portion thereof while allowing space between the edges of the recess and the needle cartridge along a top portion of the needle cartridge.

8. A container as claimed in claim 1, wherein at least one recess is provided with a drain port in the bottom thereof to permit liquids to drain out of said structure via the drain port.

9. A container as claimed in claim 8, wherein the structure further comprises a circumferential shoulder on a bottom surface of the structure which provides spacing between a top surface of a bottom of said first portion and the bottom surface of the structure.

10. A container as claimed in claim 2, wherein the basket is sterilizable.

* * * * *

UNITED STATES PATENT AND TRADEMARK OFFICE
CERTIFICATE OF CORRECTION

PATENT NO.    : 6,472,675 B2
DATED         : October 29, 2002
INVENTOR(S)   : White et al.

It is certified that error appears in the above-identified patent and that said Letters Patent is hereby corrected as shown below:

Column 6,
Line 39, please change "position" to -- portion --.
Line 57, please change "reasonably" to -- releasably --.

Signed and Sealed this

Fifth Day of August, 2003

JAMES E. ROGAN
*Director of the United States Patent and Trademark Office*

Disclaimer 6,472,675—Jack White, Alpharetta, GA. (US); John R. Vinson, Decatur, GA. (US). CONTAINER FOR STORING AND SHIPPING NEEDLE CARTRIDGES. Patent dated Oct. 29, 2002. Disclaimer filed Apr. 30, 2004, by the Assignee, Theragenics Corp.

The term of this patent shall not extend beyond the expiration date of Pat. No. 6,323,501; 6,531,705; and 6,664,555.

*(Official Gazette March 15, 2005)*